(12) United States Patent
Mozdzierz et al.

(10) Patent No.: US 10,463,373 B2
(45) Date of Patent: Nov. 5, 2019

(54) POWERED STAPLING APPARATUS

(71) Applicant: Covidien LP, Mansfield, MA (US)

(72) Inventors: Patrick Mozdzierz, Glastonbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 15/419,068

(22) Filed: Jan. 30, 2017

(65) Prior Publication Data

US 2017/0135697 A1 May 18, 2017

Related U.S. Application Data

(63) Continuation of application No. 14/197,817, filed on Mar. 5, 2014, now Pat. No. 9,592,056.

(60) Provisional application No. 61/781,487, filed on Mar. 14, 2013.

(51) Int. Cl.
*A61B 17/115* (2006.01)
*A61B 17/072* (2006.01)
*A61B 90/00* (2016.01)

(52) U.S. Cl.
CPC .... *A61B 17/1155* (2013.01); *A61B 17/07207* (2013.01); *A61B 2017/07271* (2013.01); *A61B 2090/064* (2016.02); *A61B 2090/065* (2016.02)

(58) Field of Classification Search
CPC .. A61B 17/1155; A61B 17/072; A61B 17/068
USPC .......... 227/175.1, 176.1, 19, 180.1
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

Chinese Second Office Action corresponding to counterpart Chinese Patent Appln. No. CN 2014100965550 dated Jan. 30, 2018.

(Continued)

*Primary Examiner* — Nathaniel C Chukwurah

(57) ABSTRACT

A stapler is provided. The stapler includes a handle assembly and a shaft extending distally from the handle assembly. A tool assembly is configured to selectively couple to the shaft and includes a cartridge assembly and an anvil assembly. The cartridge assembly includes a staple guide defining a tissue contacting surface. A resilient member operably positioned within the cartridge assembly is configured to bias the staple guide distally to provide a predetermined compressive force against tissue when the cartridge assembly and anvil are approximated toward one another.

18 Claims, 3 Drawing Sheets

(56) References Cited

U.S. PATENT DOCUMENTS

| | | | |
|---|---|---|---|
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A * | 5/1994 | Welch ............... A61B 17/0218 128/898 |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,484,095 A | 1/1996 | Green et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |

(56) References Cited

U.S. PATENT DOCUMENTS

| | | |
|---|---|---|
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B2 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 * | 5/2009 | Harari ............... A61B 17/0643 227/179.1 |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |

(56) References Cited

U.S. PATENT DOCUMENTS

| | | | |
|---|---|---|---|
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,740,038 B2 | 6/2014 | Shelton, IV et al. |
| 9,592,056 B2 * | 3/2017 | Mozdzierz ......... A61B 17/1155 |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0270790 A1 * | 11/2007 | Smith ................ A61B 17/1114 606/32 |
| 2008/0015617 A1 | 1/2008 | Harari et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0174099 A1 | 7/2011 | Ross et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0228358 A1 | 9/2012 | Zemlok et al. |
| 2012/0241499 A1 | 9/2012 | Baxter, III et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2-501273 B2 | 10/1990 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |
| WO | 2012/148664 A2 | 11/2012 |

OTHER PUBLICATIONS

Australian Examination Report No. 1 corresponding to counterpart Australian Patent Application No. AU 2014201345 dated Nov. 1, 2017.

Chinese Third Office Action corresponding to counterpart Patent Appln. No. CN 2014100965550 dated Aug. 17, 2018.

Chinese Office Action issued in corresponding Application No. 2014100965550, dated May 10, 2017, 16 pages w/ English abstract.

Japanese Office Action corresponding to counterpart Int'l Appln. No. JP 2014-050370 dated Nov. 20, 2017.

European Office Action corresponding to EP 14 161 175.6 dated Mar. 17, 2015; 4 pages.

U.S. Appl. No. 13/739,246, filed Jan. 11, 2013, Penna.

Extended European Search Report corresponding to EP 14 16 1175.6, completed Sep. 15, 2014 and dated Sep. 23, 2014; (5 pp).

European Office Action corresponding to EP 14 161 175.6 dated Nov. 6, 2015; 4 pp.

(56) References Cited

OTHER PUBLICATIONS

European Office Action dated Nov. 8, 2016 in corresponding European Patent Application No. 14161175, 4 pages.

* cited by examiner

POWERED STAPLING APPARATUS

CROSS-REFERENCE TO RELATED APPLICATIONS

This application is a continuation of U.S. patent application Ser. No. 14/197,817, filed Mar. 5, 2014 (now U.S. Pat. No. 9,592,056), which claims the benefit of and priority to U.S. Provisional Patent Application No. 61/781,487, filed Mar. 14, 2013, the entire contents of each of which are hereby incorporated by reference.

BACKGROUND

Technical Field

The present disclosure relates to a powered stapling apparatus. More particularly, the present disclosure relates to a powered stapling apparatus including a spring loaded cartridge assembly configured to provide a consistent and specific compressive force for stapling tissue.

Description of Related Art

Powered staplers are known, as are their use in closed procedures, i.e., endoscopic, laparoscopic or through natural body orifices. The powered staplers may include a tool assembly that is configured to operably couple to a distal end of an elongate body that extends from a handle assembly. The handle assembly is reusable and the tool assembly is, typically, disposable. The tool assembly may include an anvil assembly and a cartridge assembly that houses one or more staples therein. In use, the anvil and cartridge assemblies are approximated toward one another and the staple(s) are ejected from the cartridge assembly into the anvil assembly to form the staple(s) in tissue.

A motor powered by one or more suitable power sources (e.g., battery, outlet, etc.) may be utilized to effectuate ejecting the staple(s). One or more safe guards are typically utilized to ensure that the motor does not draw too much current. For example, prior to ejecting the staple(s), a microcontroller may be provided in the handle assembly and utilized to measure the amount of current that is being drawn from the power source by the motor. The microcontroller utilizes this current measurement to ensure that the motor does not draw an excessive amount of current which could cause damage to one or more component of the circular stapler.

As noted above, the handle assembly may be reusable. In this respect, the handle may be sterilized and re-used. As can be appreciated, the handle assembly and/or operative components associated therewith that are operable to effectuate movement of the anvil and cartridge assemblies (e.g., gears, links, etc.) may become worn and/or compromised as a result of the sterilization process and/or prolonged use of the handle assembly; this may result in these components not functioning in a manner as intended.

Conventional microcontrollers may not be configured to or capable of testing increased or decreased operational efficacy of the handle assembly and/or operative components associated therewith to determine if the handle assembly and/or operative components associated therewith are in proper working order.

SUMMARY

As can be appreciated, a powered stapling apparatus that includes a spring loaded cartridge assembly configured to provide a consistent and specific compressive force for stapling tissue may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An embodiment of the instant disclosure provides a circular stapler. The circular stapler can include a handle assembly. A shaft may extend distally from the handle assembly. A tool assembly may be configured to selectively couple to the shaft and includes a cartridge assembly and an anvil assembly. The cartridge assembly may include a staple guide defining a tissue contacting surface. A resilient member may be operably positioned within the cartridge assembly and configured to bias the staple guide distally; this provides a predetermined compressive force against tissue when the cartridge assembly and anvil are approximated toward one another.

The resilient member may couple to an underside of the tissue contacting surface of the staple guide. The resilient member may be a wave spring or a compression spring. The resilient member may be shaped to complement the tissue contacting surface of the staple guide. The staple guide may be movable with respect to the tool assembly along a longitudinal axis defined therethrough.

A microcontroller may be configured to operably communicate with a motor, for example in the handle assembly (or shaft) and a power source that is configured to energize the motor. The microcontroller may be in operable communication with the cartridge assembly and configured to test a spring constant of the resilient member.

The cartridge assembly may be configured to move through a test stroke for testing the spring constant of the resilient member. In this instance, the microcontroller may be configured to compare a tested spring constant with known spring constants compiled in a data look-up table that is stored in memory and accessible to the microcontroller. Moreover, the microcontroller may control an amount of current that is supplied to the motor based on the tested spring constant of the spring.

An embodiment of the instant disclosure provides a tool assembly that is adapted to selectively couple to handle assembly. The tool assembly includes a cartridge assembly and an anvil assembly. The cartridge assembly includes a staple guide defining a tissue contacting surface and a plurality of staple retaining slots therein. A resilient member operably positioned within the cartridge assembly is configured to bias the staple guide distally; this provides a predetermined compressive force against tissue when the cartridge assembly and anvil are approximated toward one another via the handle assembly.

The resilient member may couple to an underside of the tissue contacting surface of the staple guide. The resilient member may be a wave spring or a compression spring. The resilient member may be shaped to complement the tissue contacting surface of the guide. The staple guide may be movable with respect the tool assembly along a longitudinal axis defined therethrough.

An embodiment of the instant disclosure provides a method for stapling tissue. A handle assembly and a tool assembly are provided. The tool assembly is configured to operably couple to the handle assembly and includes a cartridge assembly, an anvil assembly and a resilient member. A wave spring or compression spring may be utilized for the resilient member. The resilient member is operably positioned within the cartridge assembly and configured to bias a staple guide of the cartridge assembly distally to provide a predetermined compressive force against tissue. The tool assembly is coupled to the handle assembly. A test stroke for testing a spring constant of the resilient member is then performed. In this instance, an amount of current that is supplied to a motor of the handle assembly is adjusted based on the tested spring constant of the spring. The cartridge assembly and anvil are then approximated toward one another and tissue is stapled.

The handle assembly may be provided with a microcontroller that is configured to operably communicate with a motor, for example in the handle assembly and a power source may be configured to energize the motor. A tested spring constant may be compared with known spring constants compiled in a data look-up table that is stored in a memory and is accessible to the microcontroller. When the spring constant is above a predetermined threshold, the amount of current that is supplied to the motor may be increased. And, when the spring constant is below a predetermined threshold, the amount of current to the motor may be decreased.

BRIEF DESCRIPTION OF THE DRAWING

The foregoing features of the invention will be more readily understood by reference to the following detailed description, taken with reference to the accompanying drawings, in which.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
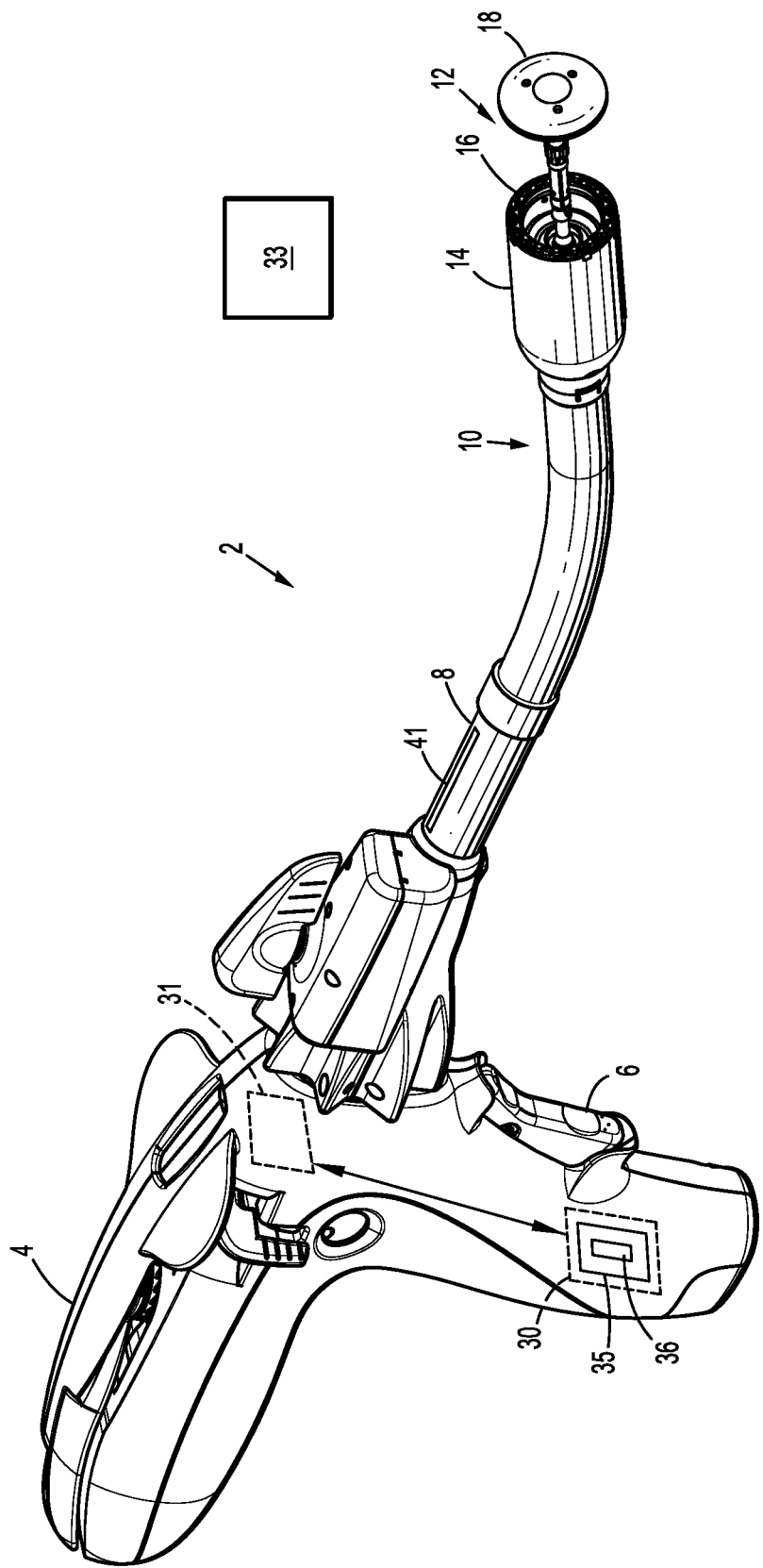
FIG. 1 is a perspective view of a handle assembly coupled to a circular tool assembly configured to perform circular anastomosis in accordance with an embodiment of the invention.
Figure 2:
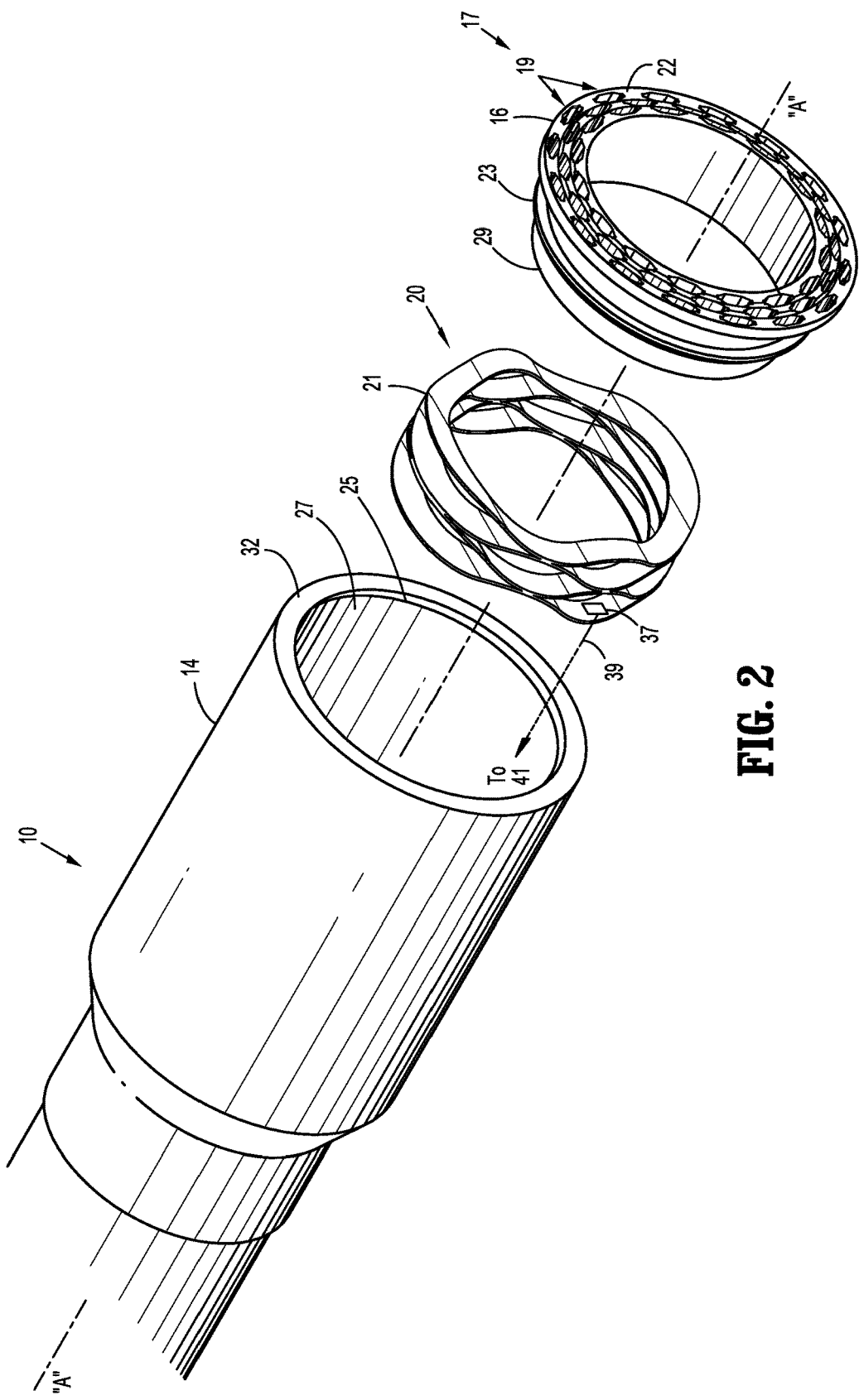
FIG. 2 is a partial, perspective view of a distal end of the circular tool assembly of FIG. 1 with parts separated in accordance with an embodiment of the invention.

In accordance with an embodiment of the invention, FIG. 1 illustrates a powered circular stapling apparatus, i.e., a stapler, shown generally as reference numeral 2. Stapler 2 includes a housing or handle assembly 4 having an actuator 6 and an elongated member, e.g., a shaft 8, extending from handle assembly 4. A tool assembly 10 (e.g., a multi-use loading unit, "MULU") is configured to operably couple to a distal end of elongated member 8 and includes an end effector 12 at a distal en thereof. End effector 12 includes a shell assembly 14 that is configured to support a cartridge assembly 16 (FIGS. 1 and 2). Cartridge assembly 16 includes a plurality of fasteners (not shown) and a corresponding plurality of pusher members (not shown) that are operatively coupled to the fastener(s). End effector 12 includes an anvil assembly 18 that is configured to releasably couple to tool assembly 10 and includes a plurality of staple forming pockets or depressions (not shown) that are configured to receive the corresponding fastener(s) therein when the fastener(s) are deployed from cartridge assembly 16.

Reference is made to U.S. Patent Application Ser. No. 61/774,071, filed on Mar. 7, 2013, entitled "CIRCULAR STAPLING DEVICE INCLUDING BUTTRESS RELEASE MECHANISM;" U.S. patent application Ser. No. 13/739,246, filed on Jan. 11, 2013, entitled "Circular Stapling Instrument;" and U.S. patent application Ser. No. 12/946,082, filed Nov. 15, 2010, entitled "Adapters for Use Between Surgical Handle Assembly and Surgical End Effector;" the entire contents of each of which are hereby incorporated by reference.

Making reference to FIG. 2, cartridge assembly 16 includes a staple guide 17 defining a tissue contacting surface 22 and a plurality of slots 19, formed in tissue contacting surface 22, that are aligned with the fastener(s) and pusher(s) thereof. Slots 19 are aligned with the staple forming pockets on anvil assembly 18 and are configured to allow the fastener(s) to deploy from cartridge assembly 16 through tissue and into the staple forming pockets of anvil assembly 18.

As the fastener(s) engage the staple-forming pockets of anvil assembly 18, the fastener(s) is/are formed and fasten tissue closed or to adjacent tissue. In an embodiment of the invention, staple guide 17 is movable with respect tool assembly 10 along a longitudinal axis "A-A" defined through tool assembly 10.

Figure 3:
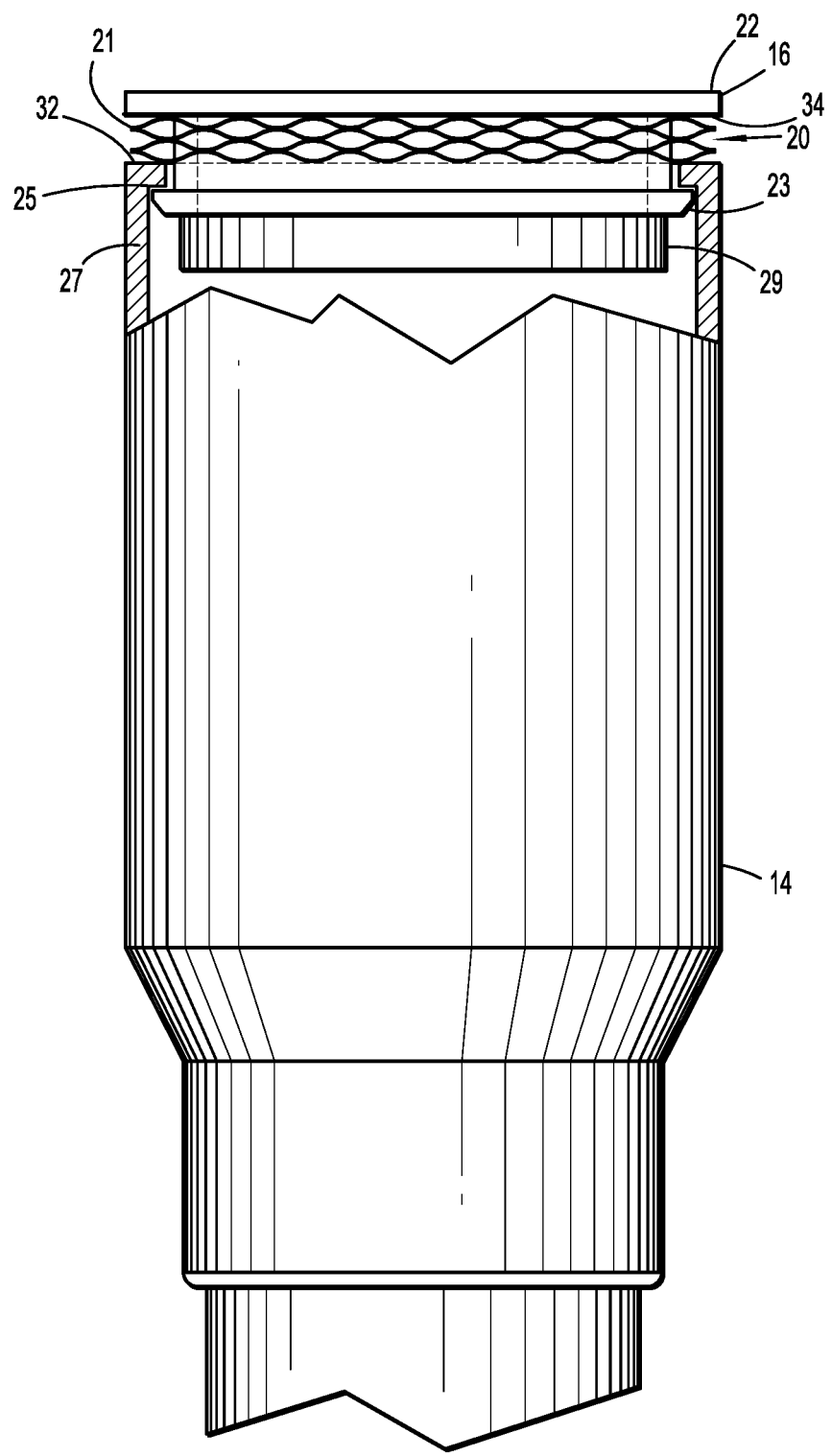
FIG. 3 is a partial, cut-away view of the distal end of the circular tool assembly in accordance with an embodiment of the invention.

As seen in FIGS. 2 and 3, a circular lip or flange 23 may be provided on a bottom circumferential wall 29 provided beneath tissue contacting surface 22 and is configured to engage a circular lip or flange 25 that extends along an inner wall 27 of shell assembly 14. In the illustrated embodiment, staple guide 17 is non-removably coupled to shell assembly 14. In an embodiment, staple guide 17 may be configured to removably couple to shell assembly 14. In an embodiment, flange 23 may be replaced with one or more relatively resilient fingers (not shown) that are configured to flex radially inwardly so as to allow a user to couple and uncouple staple guide 17 from shell assembly 14. In this coupled configuration, the resilient finger(s) may be accessible to a user such that a user may press the finger(s) inwardly to release cartridge assembly 16 from shell 14. In an embodiment, flange 23 may be replaced with one or more tabs or projections (not shown) extending radially outward from circumferential wall 29. In an embodiment, circular lip or flange 25 may be replaced with one or more tabs or projections (not shown) extending inwardly from inner wall 27 of shell assembly 14.

With continued reference to FIGS. 2-3, cartridge assembly 16 includes a resilient member 20, e.g., a wave, compression, or coil, spring 21 (hereinafter spring 21). It is also envisioned that resilient member 20 may be any material capable of deforming under pressure or force and subsequently regaining its shape or part of its shape. Specifically, spring 21 is configured to bias tissue staple guide 17 of cartridge assembly 16 outwardly or distally so as to provide a predetermined compressive force against tissue when cartridge assembly 16 and anvil assembly 18 are approximated toward one another.

Prior to use, the handle assembly 4 and tool assembly 10 perform an empty calibration clamp stroke (e.g., with no tissue positioned between the cartridge assembly 16 and anvil assembly 18) to establish a needed clamping stroke of the cartridge assembly 16 and anvil assembly 18 (e.g., with tissue positioned between the cartridge assembly 16 and anvil assembly 18). In accordance with the instant disclosure, this calibration clamp stroke fully compress the spring 21, enabling the handle assembly 4 to correctly associate current to force regardless of the age or number of cycles of the components (e.g., adapters, gears, motor, etc) on the stapler 2 and utilized to fire the stapler 2. Upon clamping the stapler 2 on tissue, the spring 21 may be compressed partially or completely if the compressive forces exceed the spring force of the spring 21. In either instance, the stapler 2 would be capable of measuring the correct target compression of captured tissues to deliver a staple crimped to contain the optimally compressed tissue.

In an embodiment, spring 21 is seated around circumferential wall 29 and positioned between an underside 34 of tissue contacting surface 22 and a distal face 22 of shell 14. In an assembled configuration, spring 21 rests against underside 34 and distal face 22, as best seen in FIG. 3. In an embodiment, spring 21 extends entirely around circumferential wall 29. In an embodiment, spring 21 extends only partially around circumferential wall 29. In an embodiment, spring 21 may be shaped (e.g., with a generally circular or curved configuration) to complement the circular configuration of tissue contacting surface 22 and circumferential wall 29 of cartridge assembly 16.

The spring 21 may disposed on or contained within other components that are configured to establish a compressive load on the tissue. For example, while the spring 21 has been described herein as being disposed within the cartridge assembly 16, the spring 21 may disposed on or contained in the anvil assembly 18, the handle assembly 4, tool assembly 10 and/or adapters (not shown) configured for use with the stapler 2.

With reference again to FIG. 1, a microcontroller 30 (shown in phantom) is configured to operably communicate with a motor 31 (shown in phantom) of handle assembly 4 and a power source 33 that is configured to energize motor 31. In embodiments, such as the illustrated embodiment, the microcontroller 30 may be housed within the handle assembly 4. In embodiments, the microcontroller 30 may be housed in the elongated member 8. Power source 33 may be any suitable power source including but not limited to a battery (rechargeable and/or non-rechargeable) or AC wall outlet.

The gearing and/or motors in the handle assembly 4 and tool assembly 10 translate the motor's 31 power into torque. As noted above, with conventional staplers, many cycles of use, and the gearing and/or motors in the handle assembly and tool assembly may "wear in" resulting in increased efficiency of current to torque. As cycling continues one or more of the gearing and/or motors, may start to degrade in their performance showing a loss of efficiency. If the efficiency of the gearing changes, the current to pressure relationship, control of pressure may also change.

As can be appreciated, it may prove advantageous to monitor and control pressure at the tissue when tissue is being stapled. In accordance therewith, the spring 21 exhibits a constant and unchanging force curve regardless of the number of cycles. Specifically, the handle assembly 4 monitors and controls current input into the motor 31. Thus, by calibrating the cartridge assembly 16 and anvil assembly 18 against the spring 21, the microcontroller 30 may set to a value of current that corresponds to a force of a spring constant to be the assigned value of the spring 21. Thus, when the stapler 2 is cycled through a clamping and stapling stroke, the current that the microcontroller is reading, monitoring, and controlling can be controlled for in terms of force as opposed to current.

Microcontroller 30 may be in operable communication with cartridge assembly 16 and configured to test a spring constant of spring 21. Specifically, microcontroller 30 may be configured to compare a tested spring constant with known spring constants that are compiled in one or more data look-up tables 36 and stored in memory 35 (shown in phantom) that is accessible by microcontroller 30. The known spring constants may be acquired through measurement of a range of different resilient members that may be utilized with cartridge assembly 16.

In embodiments, application software that is executable by the microcontroller 30 may be utilized to calculate a desired force. In such an embodiment, tool assembly 10 may include an identification chip or electrically erasable programmable read-only memory device (EEPROM) which will communicate with the microcontroller 30. Information on the tool assembly 10 may include, for example, staple sizes, tool assembly type, etc., and the spring type/load can be communicated to the handle assembly 4 to enable the application software to establish running parameters of current to actual forces. Additionally or alternatively, a separate spring loaded device (not explicitly shown) may be used to interpose between the anvil assembly 18 and a staple guide of the tool assembly 10 to establish the necessary force to current relationship.

In an embodiment, memory 35 may be a module or component of microcontroller 30. Memory 35 may be any suitable computer readable medium and may include both volatile and/or nonvolatile memory and data storage components. Memory 35 may include, for example, random access memory (RAM) and/or read-only memory (ROM). The RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), an EEPROM, and other like memory device.

One or more sensors 37 (or other suitable device(s)) may be operably coupled to spring 21 and are configured to measure a spring constant of spring 21 (FIG. 2). Sensor(s) 37 may be a force transducer, accelerometer, or other suitable sensor. In an embodiment, cable 39 (wire or the like) may extend through tool assembly 10 and may be configured to couple to a corresponding cable 41 (FIG. 1). Cable 41 extends through elongated shaft 8 and couples to microcontroller 30 for communication therewith.

In an embodiment, cartridge assembly 16 is configured to move through a test or calibration stroke for testing a spring constant of spring 21. Specifically, microcontroller 30 controls an amount of current that is supplied to motor 31 based on the tested spring constant of spring 21. More specifically, microcontroller 30 provides more current to motor 31 when the spring constant is above a predetermined threshold and provides less current to motor 31 when the spring constant is below a predetermined threshold.

In use, tool assembly 10 may be coupled to elongated shaft 8. Thereafter, a test stroke for testing a spring constant of spring 21 may be performed. During the test stroke, anvil 18 is approximated a predetermined distance towards cartridge assembly 16 against the bias of spring 21. Subsequently, microcontroller 30 may utilize one or more suitable control algorithms to determine the spring constant of spring 21.

Thereafter, microcontroller 30 accesses data look-up table 36 in memory 33 and compares the determined spring constant with the known spring constants of data look-up table 36. Microcontroller 30 provides more current to motor 31 if the spring constant is above a predetermined threshold and provides less current to motor 31 if the spring constant is below a predetermined threshold.

As can be appreciated, utilization of microcontroller 30 and sensor 37 to determine a spring constant of spring 21 that is coupled to cartridge assembly 16 overcomes the aforementioned drawbacks that may be associated with conventional circular anastomosis staplers. Specifically, microcontroller 30, through the test or calibration stroke, can detect degradation of handle assembly 4 and/or operative components associated therewith. As can be appreciated, this may extend the operable shelf life of stapler 2 and/or tool assembly 10.

Thereafter, tissue can be positioned between the tissue contacting surface 22 of the cartridge assembly 16 and the anvil assembly 18 and then the anvil assembly 18 may be approximated towards the tissue contacting surface 22 of the cartridge assembly 16. Actuator 6 may then be actuated to staple the tissue.

Current stapling is done based upon experienced surgeons choosing a cartridge with a set staple height. Incorrect estimation of tissue thickness versus cartridge selection can lead to either: tissue insufficiently compressed leading to bleeding and/or dehiscence and leakages or over compressed tissue which may damage serosal/mucosal membranes and even potentials results in ischemic tissue.

In accordance with the instant disclosure, however, a predetermined clamping force is established to increase/decrease the clamping force of the cartridge assembly 16 and anvil assembly 18 that are holding tissue in place before staples are fired to maintain a specific clamping force. As can be appreciated, to be able to provide a surgeon with clamping information and suggested ranges, will enable the surgeon to use that information and, if need be, tweak compression between the cartridge assembly 16 and anvil assembly 18 prior to stapling tissue.

From the foregoing and with reference to the various figure drawings, those skilled in the art will appreciate that certain modifications can also be made to the present disclosure without departing from the scope of the same. For example, while the microcontroller 30, spring 21 and sensor 37 have been described herein configured for use with a circular stapler 2, the microcontroller 30, spring 21 and sensor 37 may be configured for use with other types of staplers, e.g., linear stapling devices, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tool assembly adapted to selectively couple to a handle assembly, the tool assembly comprising:
   a cartridge assembly and an anvil assembly, the cartridge assembly including and supporting a staple guide defining a tissue contacting surface and a plurality of staple retaining slots;
   a resilient member operably positioned within the cartridge assembly and configured to bias the staple guide distally to provide a predetermined compressive force against tissue when the cartridge assembly and the anvil assembly are approximated toward one another; and
   a sensor disposed on a surface of the resilient member configured to measure a spring constant of the resilient member.

2. A tool assembly according to claim 1, further comprising a shell assembly defining an inner surface, the inner surface of the shell assembly configured to support the cartridge assembly.

3. A tool assembly according to claim 2, wherein the shell assembly includes a circumferential flange at a distal end thereof, the circumferential flange extending radially inward from the inner surface of the shell assembly.

4. A tool assembly according to claim 3, wherein the resilient member is disposed between an underside of the tissue contacting surface of the staple guide and the circumferential flange of the shell assembly.

5. A tool assembly according to claim 4, wherein the resilient member couples to the underside of the tissue contacting surface of the staple guide.

6. A tool assembly according to claim 3, wherein the staple guide includes a circumferential wall at a proximal end portion thereof and the tissue contacting surface at a distal end portion thereof.

7. A tool assembly according to claim 6, further including a circular lip disposed between the circumferential wall and the tissue contacting surface of the staple guide, the circular lip configured to engage a surface of the circumferential flange of the shell assembly to couple the staple guide to the tool assembly.

8. A tool assembly according to claim 1, wherein the resilient member is one of a wave spring and a compression spring.

9. A tool assembly according to claim 1, wherein the resilient member is shaped to complement the tissue contacting surface of the staple guide.

10. A tool assembly according to claim 1, wherein the staple guide is movable with respect the tool assembly along a longitudinal axis defined therethrough.

11. A tool assembly according to claim 1, wherein the sensor is selected from the group consisting of a force transducer and an accelerometer.

12. A stapler, comprising:
   a handle assembly;
   a shaft extending distally from the handle assembly;
   a tool assembly coupled to the shaft and including a cartridge assembly and an anvil assembly, the cartridge assembly including and supporting a staple guide defining a tissue contacting surface and a plurality of staple retaining slots;
   a resilient member operably positioned within the cartridge assembly and configured to bias the staple guide distally to provide a predetermined compressive force against tissue when the cartridge assembly and the anvil assembly are approximated toward one another; and
   a sensor disposed on a surface of the resilient member configured to measure a spring constant of the resilient member.

13. A stapler according to claim 12, further comprising a shell assembly defining an inner surface, the inner surface of the shell assembly configured to support the cartridge assembly.

14. A stapler according to claim 13, wherein the shell assembly includes a circumferential flange at the distal end thereof, the circumferential flange extending radially inward from the inner surface of the shell assembly.

15. A stapler according to claim 14, wherein the resilient member is disposed between an underside of the tissue contacting surface of the staple guide and the circumferential flange of the shell assembly.

16. A stapler according to claim 14, wherein the staple guide includes a circumferential wall at a proximal end portion thereof and the tissue contacting surface at a distal end portion thereof.

17. A stapler according to claim 16, further including a circular lip disposed between the circumferential wall and the tissue contacting surface of the staple guide, the circular lip configured to engage a surface of the circumferential flange of the shell assembly to couple the staple guide to the tool assembly.

18. A stapler according to claim 12, further comprising a microcontroller configured to operably communicate with the sensor, the microcontroller and the sensor in operable communication with the cartridge assembly.

* * * * *